United States Patent
Diga et al.

(10) Patent No.: US 12,047,456 B2
(45) Date of Patent: *Jul. 23, 2024

(54) MANAGING COMMUNICATIONS WITH A CONNECTED HEALTH SYSTEM

(71) Applicants: Fresenius Medical Care Deutschland GmbH, Bad Homburg (DE); Fresenius Medical Care Holdings, Inc., Waltham, MA (US)

(72) Inventors: Mihai Diga, Bad Homburg (DE); Klaus Wolf, Bad Homburg (DE); Stefan Perplies, Bad Homburg (DE); Karsten Fischer, Waltham, MA (US); Johannes Thoelking, Bad Homburg (DE)

(73) Assignees: Fresenius Medical Care Deutschland GmbH; Fresenius Medical Care Holdings, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/037,392

(22) PCT Filed: Nov. 9, 2021

(86) PCT No.: PCT/US2021/058515
§ 371 (c)(1),
(2) Date: May 17, 2023

(87) PCT Pub. No.: WO2022/108782
PCT Pub. Date: May 27, 2022

(65) Prior Publication Data
US 2024/0007535 A1    Jan. 4, 2024

Related U.S. Application Data

(63) Continuation of application No. 16/951,637, filed on Nov. 18, 2020, now Pat. No. 11,394,784.

(51) Int. Cl.
*H04L 67/14* (2022.01)
*G16H 20/40* (2018.01)
(Continued)

(52) U.S. Cl.
CPC .............. *H04L 67/14* (2013.01); *G16H 20/40* (2018.01); *G16H 40/67* (2018.01); *G16H 50/20* (2018.01);
(Continued)

(58) Field of Classification Search
CPC ......... H04L 67/14; H04L 12/66; H04L 67/10; H04L 67/12; G16H 20/40; G16H 40/67; G16H 50/20
See application file for complete search history.

(56) References Cited

U.S. PATENT DOCUMENTS 10,061,899 B2    8/2018  Miller et al.
10,154,097 B2 *  12/2018  Wang ..................... G16H 40/67
(Continued)

FOREIGN PATENT DOCUMENTS

EP        1574178       9/2005
WO   WO 2007/126360    11/2007
(Continued)

OTHER PUBLICATIONS

International Search Report and Written Opinion in International Appln. No. PCT/US2021/058515, mailed Feb. 3, 2022, 13 pages.
(Continued)

*Primary Examiner* — Abdullahi E Salad
(74) *Attorney, Agent, or Firm* — Fish & Richardson P.C.

(57) ABSTRACT

A medical system, comprising: a medical machine; and a gateway device configured to communicate with the medical machine to allow access to a network, the gateway device comprising a data allowance and limitation unit that is configured to limit communication between the medical machine and the network when the data allowance and limitation unit is in an open state, wherein the data allowance and limitation unit is placed in the open state when a plannable system event occurs, and wherein, while in the
(Continued)

open state, the data allowance and limitation unit is placed in a closed state when an unplanned event occurs, thereby providing less limited communication between the medical machine and the network compared to the open state.

20 Claims, 5 Drawing Sheets

(51) Int. Cl.
    *G16H 40/67*     (2018.01)
    *G16H 50/20*     (2018.01)
    *H04L 12/66*     (2006.01)
    *H04L 67/10*     (2022.01)
    *H04L 67/12*     (2022.01)

(52) U.S. Cl.
    CPC .............. *H04L 12/66* (2013.01); *H04L 67/10* (2013.01); *H04L 67/12* (2013.01)

(56) References Cited

U.S. PATENT DOCUMENTS

| | | | | |
|---|---|---|---|---|
| 10,322,225 | B2* | 6/2019 | Kotsos | ................... H04B 7/08 |
| 10,404,803 | B2* | 9/2019 | Wang | ................... H04L 67/125 |
| 2006/0036555 | A1* | 2/2006 | Beck | ................... G16H 40/40 705/75 |
| 2013/0193041 | A1 | 8/2013 | Rohde | |
| 2013/0310726 | A1* | 11/2013 | Miller | ................... G16H 20/17 717/173 |
| 2016/0022926 | A1* | 1/2016 | Peatfield | ........... A61M 5/16854 604/506 |
| 2017/0228520 | A1* | 8/2017 | Kidd | ................... G16H 20/13 |
| 2019/0327584 | A1* | 10/2019 | Plahey | ................... H04W 4/12 |
| 2020/0086025 | A1 | 3/2020 | Marterstock | |
| 2020/0222609 | A1 | 7/2020 | Ballantyne et al. | |
| 2020/0253477 | A1* | 8/2020 | Freeman | ................ G16H 50/20 |
| 2020/0357513 | A1* | 11/2020 | Katra | ................... G16H 40/63 |

FOREIGN PATENT DOCUMENTS

WO    WO 2009/136243    11/2009
WO    WO 2013/074635    5/2013

OTHER PUBLICATIONS

Wang et al., "Using convolutional neural networks to identify patient safety incident reports by type and severity," Journal of the American Medical Informatics Association, Dec. 2019, 26(12):1600-1608, 9 pages.

* cited by examiner

MANAGING COMMUNICATIONS WITH A CONNECTED HEALTH SYSTEM

TECHNICAL FIELD

This disclosure relates to managing communications with a connected health system.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

Dialysis machines are typically equipped with interfaces for receiving inputs and providing information to users. Dialysis machines are also typically equipped with data communication capabilities.

SUMMARY

In an aspect, a medical system includes a medical machine, and a gateway device configured to communicate with the medical machine to allow access to a network, the gateway device comprising a data allowance and limitation unit that is configured to limit communication between the medical machine and the network when the data allowance and limitation unit is in an open state, wherein the data allowance and limitation unit is placed in the open state when a plannable system event occurs, and wherein the data allowance and limitation unit is placed in a closed state when an unplanned event occurs, thereby providing less limited communication between the medical machine and the network compared to the open state.

Implementations can include one or more of the following features.

In some implementations, the data allowance and limitation unit is a hardware switch.

In some implementations, the data allowance and limitation unit is physically controllable.

In some implementations, the data allowance and limitation unit is electronically controllable.

In some implementations, the plannable system event includes one or more of connecting a patient to the medical system, providing medical therapy by the medical system, or connecting or installing disposable components to the medical system.

In some implementations, the unplanned event includes one or more of a patient needing further instructions for the preparation or use of the medical system, the medical system sensing a faulty use of medical equipment and recommending support by a medical professional or technician, the medical system sensing a critical health condition of the patient before, during, or after medical therapy and recommending support, the medical system sensing a technical problem, or the medical system sensing a complication potentially leading to critical health conditions of the patient.

In some implementations, the medical system is a dialysis system and the medical machine is a dialysis machine.

In some implementations, the dialysis system is a home dialysis system and the dialysis machine is a home dialysis machine.

In some implementations, the dialysis system is a hemodialysis or peritoneal dialysis system, and the dialysis machine is a hemodialysis or peritoneal dialysis machine.

In some implementations, the medical system includes a notification system.

In some implementations, when the data allowance and limitation unit is in the open state and before transitioning into the closed state, the notification system notifies a patient of the unplanned event and asks whether communication between the medical machine and the network should be enabled.

In some implementations, the notification is acoustical, optical or tactile.

In some implementations, the patient is presented with an option to accept or decline a recommendation to reestablish communication between the medical machine and the network.

In some implementations, the medical system includes a user interface through which the patient can accept or decline the recommendation to reestablish communication.

In some implementations, if the patient does not respond to the recommendation, the data allowance and limitation unit moves into the closed state and communication between the medical machine and the network is reestablished automatically.

In some implementations, the data allowance and limitation unit moves into the closed state and communication between the medical machine and the network is reestablished automatically if the medical system senses irregularities in the patient's vital parameters.

In some implementations, a patient can reestablish communication between the medical machine and the network without the unplanned event occurring.

In some implementations, the patient reestablishes communication between the medical machine and the network by interacting with a user interface of the medical system, which causes the data allowance and limitation unit to move into the closed state, or by interacting with the data allowance and limitation unit directly to cause it to move into the closed state.

In another aspect, a method performed by a medical system includes communicating, by a medical machine of the medical system, with a gateway device to allow access to a network, the gateway device comprising a data allowance and limitation unit that is configured to limit communication between the medical machine and the network when the data allowance and limitation unit is in an open state, placing the data allowance and limitation unit into the open state when a plannable system event occurs, and while in the open state, placing the data allowance and limitation unit into a closed state when an unplanned event occurs, thereby providing less limited communication between the medical machine and the network compared to the open state.

In another aspect, a method performed by a medical system includes communicating, by a medical machine of the medical system, with a gateway device to allow access to a network, the gateway device comprising a data allowance and limitation unit that is configured to prevent or limit the transmission of all data types and/or of all data sizes when the data allowance and limitation unit is in the open state and allow the transmission of all data types and/or of all data sizes when the data allowance and limitation unit is in the closed state.

In another aspect, a method performed by a medical system includes communicating, by a medical machine of the medical system, with a gateway device to allow access to a network, the gateway device comprising a data allowance and limitation unit that is configured to allow the transmission of a first subset of data types and/or data sizes when the data allowance and limitation unit is in the open state and allow the transmission of a second subset of data types and/or data sizes when the data allowance and limitation unit is in the closed state, wherein the second subset is larger than the first subset.

In another aspect, a connected health system includes a medical system. The medical system includes a medical machine, and a gateway device configured to communicate with the medical machine to allow access to a network, the gateway device comprising a data allowance and limitation unit that is configured to limit communication between the medical machine and the network when the data allowance and limitation unit is in an open state, wherein the data allowance and limitation unit is placed in the open state when a plannable system event occurs, and wherein, while in the open state, the data allowance and limitation unit is placed in a closed state when an unplanned event occurs, thereby providing less limited communication between the medical machine and the network compared to the open state. The connected health system also includes one or more remote systems.

Implementations can include one or more of the following advantages.

In some implementations, the data allowance and limitation unit is configured to prevent or limit the transmission of all data types and/or of all data sizes when the data allowance and limitation unit is in the open state and allow the transmission of all data types and/or of all data sizes when the data allowance and limitation unit is in the closed state.

In some implementations, the data allowance and limitation unit is configured to allow the transmission of a first subset of data types and/or data sizes when the data allowance and limitation unit is in the open state and allow the transmission of a second subset of data types and/or data sizes when the data allowance and limitation unit is in the closed state, wherein the second subset is larger than the first one.

In some implementations, preventing or limiting data communication during a treatment can prevent or limit unauthorized contact with the dialysis system during a plannable system event (e.g., during a planned treatment). Thus, during the treatment, and by default, data communication is disabled. During the treatment, an unplanned event may occur which may necessitate data communications. For example, an issue with respect to the treatment may arise that requires the patient to seek input from one or more external parties (e.g., a technician, a medical professional, etc.). The patient can interact with the gateway device to cause data communication to be re-enabled during the treatment. In this way, the patient can interact with the external parties to resolve the issue. Thereafter, data communication can be disabled or limited again, thereby preventing or limiting unauthorized contact with the dialysis system during the treatment.

The systems and techniques described herein empower patients to intelligently control the data communication capabilities of the dialysis system with the network using either software or hardware-based solutions. Further, the systems and techniques described herein allow the patient to reestablish data communication, which is initially cut off, during a treatment. In other words, existing systems may disable data communication during an entire treatment in such a way that data communication cannot be re-enabled, or in such a way that it can only be re-enabled by intervention from the medical professional's side. The systems and techniques described herein are not so limited, and instead allow for data communication to be disabled when a treatment commences while still allowing the patient to cause data communication to be reestablished should an unplanned system event occur.

Other aspects, features, and advantages of the invention will be apparent from the description and drawings, and from the claims.

DESCRIPTION OF DRAWINGS

Like reference symbols in the various drawings indicate like elements.

DETAILED DESCRIPTION

A medical system (e.g., a dialysis system) can include a medical machine such as a dialysis machine, which can also be a home dialysis machine, and a home gateway device in communication with a cloud-based application via a connected health system. The gateway device can communicate with one or more other systems (e.g., remote systems) via the cloud-based application. In some examples, such communications can be enabled or disabled depending on a number of factors. For example, communications may be disabled or limited during a dialysis treatment to prevent or limit unauthorized contact with the dialysis system. In some examples, communications may be enabled in response to one or more predetermined events. For example, if a health and/or safety concern arises during a dialysis treatment, communications may be re-enabled to allow for an external party to intervene.

Figure 1:
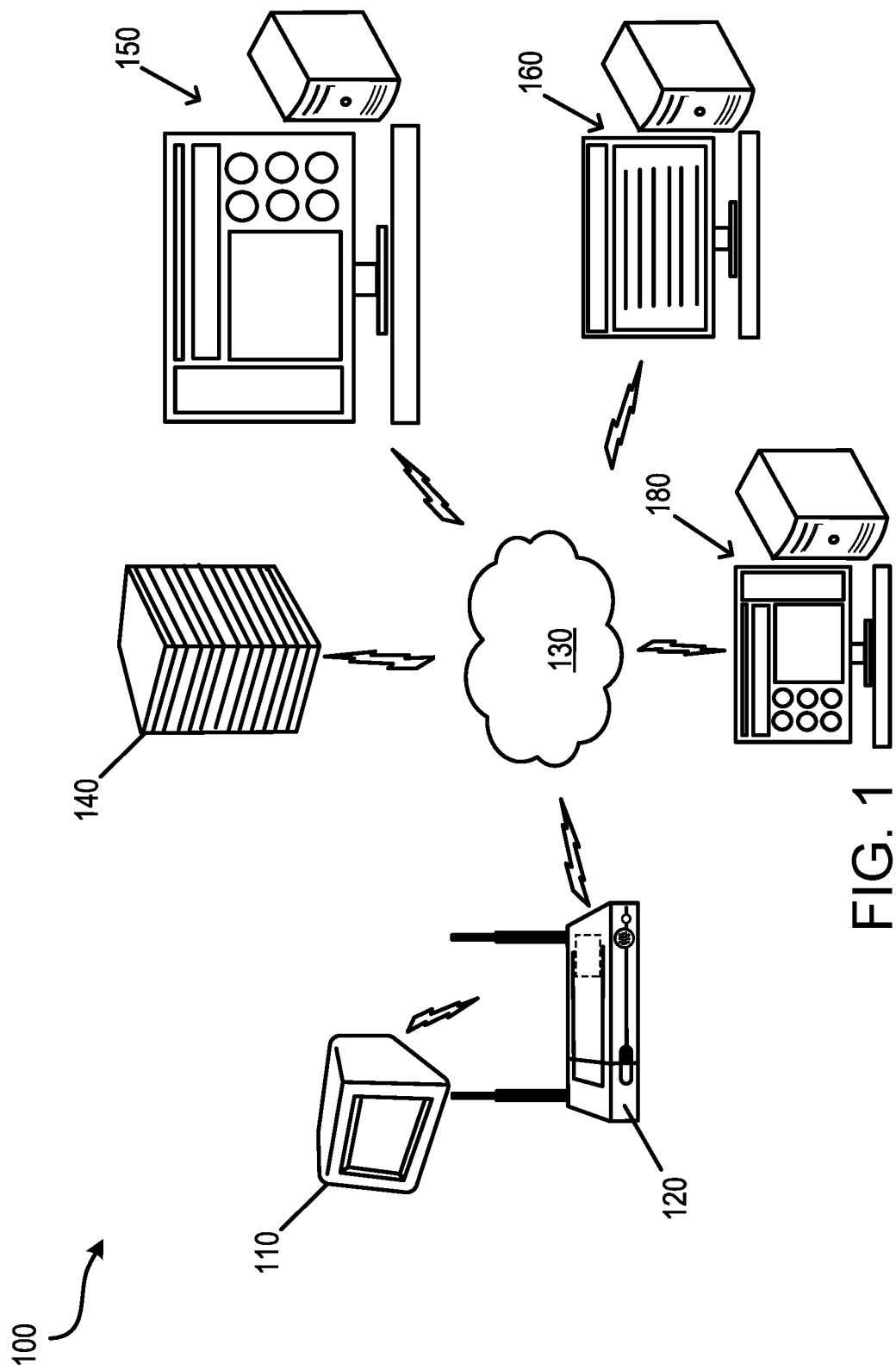
FIG. 1 is a schematic illustration showing an example of a Connected Health ("CH") system that includes a dialysis system and a gateway device.

FIG. 1 is a schematic illustration showing an example of a Connected Health ("CH") system 100 that includes, among other things, a dialysis system 110 (e.g., a home dialysis system), a gateway device 120 (e.g., a home gateway device), and a network 130 (e.g., a wide area network (WAN), such as the Internet). The gateway device 120 is configured to receive data from the dialysis system 110 and provide the data to the network 130, and receive data from the network 130 and provide the data to the dialysis system 110. The dialysis system 110 and the gateway device 120 may communicate via a wired (e.g., Ethernet) or wireless connection (e.g., WiFi, Bluetooth, etc.). The dialysis system 110 and the gateway device 120 may communicate with one or more additional systems via the network 130. The network 130 thus serves as a communication pipeline (e.g., facilitates the transfer of data) among components and systems of the CH system 100.

The CH system 100 includes one or more additional systems in communication with the network 130. In the illustrated example, the CH system 100 includes a prescription management system 140, a clinical information system 150, an operations system 160, and a technical support system 180, although additional or fewer external systems may be provided.

The prescription management system 140 and/or the clinical information system 150 is configured to facilitate the transfer of medical prescriptions to/from the dialysis system 110 via the network 130 (e.g., via the gateway device 120).

In some implementations, the clinical information system 150 is located in a clinical setting (e.g., at a clinic, hospital, etc.). The clinical information system 150 is configured to store electronic health records of patients. The electronic health records can be examined by a medical professional to manage treatment of patients, in some examples in real-time during a medical treatment. Following a treatment provided by the dialysis system 110, the dialysis system 110 (e.g., via the gateway 120) may provide treatment data and/or patient data to the clinical information system 150 via the network 130 for storage. Such treatment data and/or patient data may be considered by a medical professional when generating a prescription using the prescription management system 140 and/or the clinical information system 150.

The operations system 160 is configured to perform activation/deactivation functions for the components of the CH system 100, manage supply chain (e.g., of medical supplies), and perform asset tracking functions.

The technical support system 180 is configured to receive diagnostic information from the components and systems of the CH system 100. Technical support professionals can review such diagnostic information and use the technical support system 180 to issue commands and/or operations to the components and systems of the CH system 100. In this way, the technical support system 180 can be used for corrective action functions.

Figure 2:
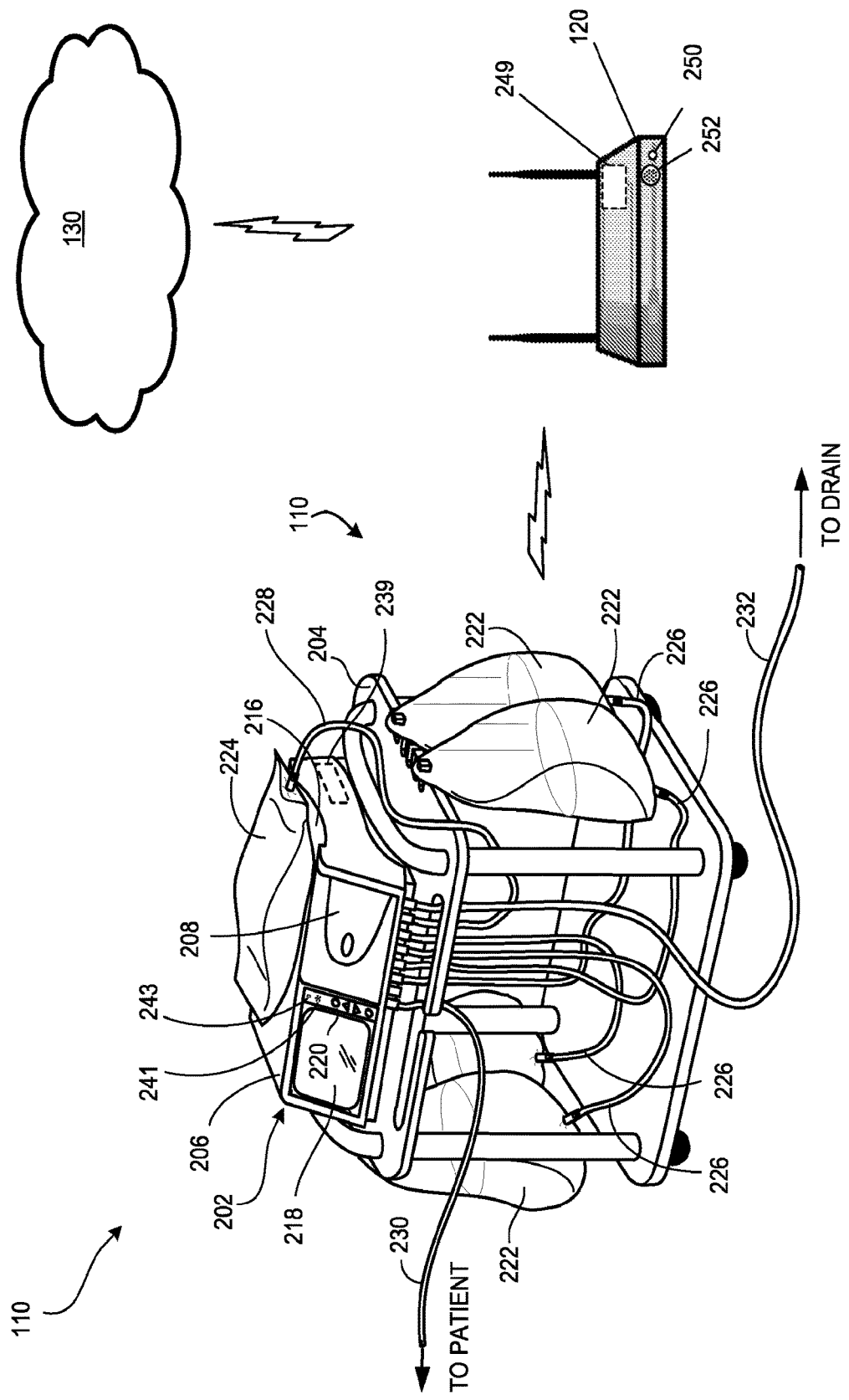
FIG. 2 shows an example of a system that includes the dialysis system and the gateway device of FIG. 1.

FIG. 2 shows an example of the dialysis system 110 and the gateway device 120 in communication with the CH cloud 130 of FIG. 1. In some implementations, the gateway device 120 itself is part of the dialysis system 110. For example, when the gateway device 120 is in communication with the dialysis system 110, or when the gateway device 120 becomes associated with the dialysis system 110 (e.g., when the gateway device 120 is first connected to the dialysis system 110), the gateway device 120 becomes part of the dialysis system 110 and is generally referred to as "belonging" to the dialysis system 110. In some implementations, the gateway device 120 may be part of the dialysis system 110 (e.g., part of the dialysis machine).

In some implementations, the dialysis system 110 is a home dialysis system. In the illustrated example, the dialysis system 110 is a peritoneal dialysis ("PD") system 110 that is configured for use in a home of a patient. It is noted that the PD system 110 is shown representationally and that other types and configurations of PD systems different than that principally described herein may be used in connection with the system described herein. The PD system 110 includes a PD machine (also referred to as a PD cycler) 202 seated on a cart 204. The PD machine 202 includes a housing 206, a door 208, and a cassette interface that contacts a disposable PD cassette when the cassette is disposed within a cassette compartment formed between the cassette interface and the closed door 208. A heater tray 216 is positioned on top of the housing 206. The heater tray 216 is sized and shaped to accommodate a bag of dialysate (e.g., a 5-liter bag of dialysate). The PD machine 202 also includes a user interface such as a touch screen display 218 and additional control buttons 220 that can be operated by a user (e.g., a caregiver or a patient) to allow, for example, set up, initiation, and/or termination of a PD treatment, as well as the medical supply ordering functions described below.

Dialysate bags 222 are suspended from fingers on the sides of the cart 204, and a heater bag 224 is positioned in the heater tray 216. The dialysate bags 222 and the heater bag 224 are connected to the cassette via dialysate bag lines 226 and a heater bag line 228, respectively. The dialysate bag lines 226 can be used to pass dialysate from dialysate bags 222 to the cassette during use, and the heater bag line 228 can be used to pass dialysate back and forth between the cassette and the heater bag 224 during use. In addition, a patient line 230 and a drain line 232 are connected to the cassette. The patient line 230 can be connected to a patient's abdomen via a catheter and can be used to pass dialysate back and forth between the cassette and the patient's peritoneal cavity during use. The drain line 232 can be connected to a drain or drain receptacle and can be used to pass dialysate from the cassette to the drain or drain receptacle during use.

The PD machine 202 also includes a control unit 239 (e.g., a processor) that is configured to receive signals from and transmit signals to the touch screen display 218, the control buttons 220, and the various other components of the PD system 110 and/or the gateway device 120. The control unit 239 is configured to control operating parameters of the PD machine 202.

The gateway device 120 is configured to communicate with the PD machine 202. In this way, the gateway device 120 can act as a communications hub (e.g., node) that allows communication between the PD machine 202 and one or more other systems and/or devices (e.g., such as those illustrated in FIG. 1) via the network 130. While the gateway device 120 is in wireless communication with the PD machine 202 in the illustrated example, the gateway device 120 and the PD machine 202 may also or alternatively be connected by a wired connection (e.g., an Ethernet cable). The gateway device 120 includes a control unit 249 (e.g., a processor), and can include a microphone 250, and a speaker 252. The gateway device 120 is configured to receive audio input (e.g., spoken words, such as commands, questions/ answers, etc.) through the microphone 250 and provide audio output (e.g., spoken words, such as questions/answers, instructions, alarms, confirmations, etc.) through the speaker 252. The control unit 249 is configured to process the audio input received through the microphone 250 and identify the spoken words. For example, the control unit 249 may include voice recognition capability that allows the control unit 249 to convert the audio input into words of a spoken language. The control unit 249 can identify questions, answers, commands, etc. formed by the recognized words.

While the gateway device 120 is described as including the microphone 250 and the speaker 252, in some implementations, the dialysis system 110 itself can include a microphone, a speaker, etc., for enabling voice recognition capabilities. Such microphone, speakers, etc. may be provided instead of or in addition to the microphone 250 and the speaker 252 of the gateway device 120.

In some implementations, communication between gateway device 120 and the dialysis system 110 can be realized via an additional device (e.g., a smartphone, a tablet, a laptop computer, etc.) where an application running on the device may forward/link data streams between the gateway device 120 and the dialysis system 110. In some implementations, the data allowance and limitation unit may be embodied as a software program running on the additional device, such that the patient can interact with the additional device to cause data communication to be enabled/disabled, as described in more detail below. In this way, interacting with the software program running on the additional device can cause data communication between the dialysis system 110 and the gateway device 120 to cease.

In some implementations, it may be desirable to disable communication capabilities of the dialysis system 110. For example, it may be desirable to prevent or limit the dialysis system 110 from communicating with external systems via the network 130. Reasons for disabling communication capabilities of the dialysis system 110 can include preventing unauthorized access to the dialysis system 110 during critical times (e.g., during a treatment). In some implementations, data communications between the dialysis system 110 and the network 130 (e.g., the Internet) may make the dialysis system 110 prone to dangerous cyberattacks. In such events, unauthorized persons or organizations with harmful intentions may access connected medical systems leading to potentially dangerous situations for patients receiving medical therapy. Therefore, at least during plannable system events, data communication between the dialysis system 110 and the network 130 can be disabled. Such plannable system events can include connecting a patient to the dialysis system 110, providing medical therapy by the dialysis system 110, and/or connecting/installing disposable components to the dialysis system 110.

In some implementations, the dialysis system 110 itself may inform about potential issues, and in turn, may automatically disable data communication capabilities when plannable system events occur.

While data communication between the dialysis system 110 and the network 130 may be disabled using software means, such strategies may be insufficient as certain types of malicious algorithms could be able to circumvent software-based protections alone, making the dialysis system 110 vulnerable in some conditions. Therefore, a hardware-based approach may be preferable in certain situations.

The systems and techniques described herein empower patients to intelligently control the data communication capabilities of the dialysis system 110 with the network 130 using either software or hardware-based solutions. Further, the systems and techniques described herein allow the patient to reestablish data communication, which is initially cut off, during a treatment. In other words, existing systems may disable data communication during an entire treatment in such a way that data communication cannot be re-enabled, or in such a way that it can only be re-enabled by intervention from the medical professional's side. The systems and techniques described herein are not so limited, and instead allow for data communication to be disabled when a treatment commences while still allowing the patient to cause data communication to be reestablished should an unplanned system event occur, as described in more detail below.

Figure 3A:
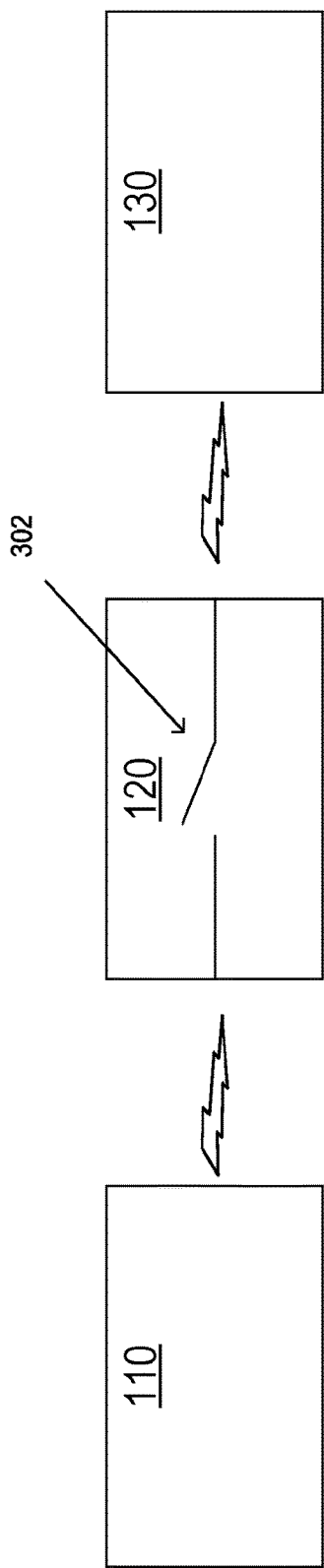
FIGS. 3A and 3B show block diagrams illustrating data communication between the dialysis system and a network via the gateway device.

FIG. 3A shows a block diagram illustrating data communication between the dialysis system 110, the gateway device 120, and the network 130, in an example implementation. Subsequent connections between the network 130 and external systems (e.g., the systems illustrated in FIG. 1) are not shown. The gateway device 120 includes a data allowance and limitation unit 302. In some implementations, the data allowance and limitation unit is a hardware switch (e.g., a physical switch). In the illustrated example, the data allowance and limitation unit 302 is shown as being in the opened state. When in the opened state, communication between the dialysis system 110 and the network 130 is physically prevented or limited. The data allowance and limitation unit 302 may be physically controllable (e.g., a toggle switch) or may be controllable by software. In some implementations, the data allowance and limitation unit 302 may be in the closed state during times when the dialysis system 110 is authorized to communicate with the network 130, such as during times when there is limited potential danger due to outside communication with the dialysis system 110. Such times could include at the conclusion of therapy, such as when treatment-related information is transmitted to one or more external systems (e.g., such as the clinical information system 150 of FIG. 1). Such times could also include before therapy, such as when a dialysis prescription is transmitted to the dialysis system 110 (e.g., from the prescription management system 140 of FIG. 1).

While a physical switch is described with respect to FIG. 3A, it should be understood that some implementations may include a software switch. That is, a connection in the gateway device 120 may not be physically severed when the data allowance and limitation unit 302 is in the open state, but instead, software running on the gateway device 120 may limit data communication when the data allowance and limitation unit 302 is in the open state.

In some implementations, the data allowance and limitation unit 302 may be implemented as a user interface element that is presented on a user interface (e.g., the touch screen display 218 of the PD machine 202, or a user interface of the gateway device 120, or a user interface of another connected device such as a smart phone or a tablet). For example, the touchscreen display 218 may present a reconnect button that causes data communication to be re-established (e.g., either immediately or after one or more other steps, as described in more detail below). In some implementations, the data allowance and limitation unit 302 may be implemented as a help button that is available during one or more phases of the pre-treatment, treatment, and post-treatment (e.g., during preparation, treatment, post-processing, etc.). Further, the data allowance and limitation unit 302 may be available during various conditions of the dialysis system 110, for example, during normal conditions (e.g., normal operation), during alarm conditions, during safe operational modes, or during malfunctional modes.

Figure 4:
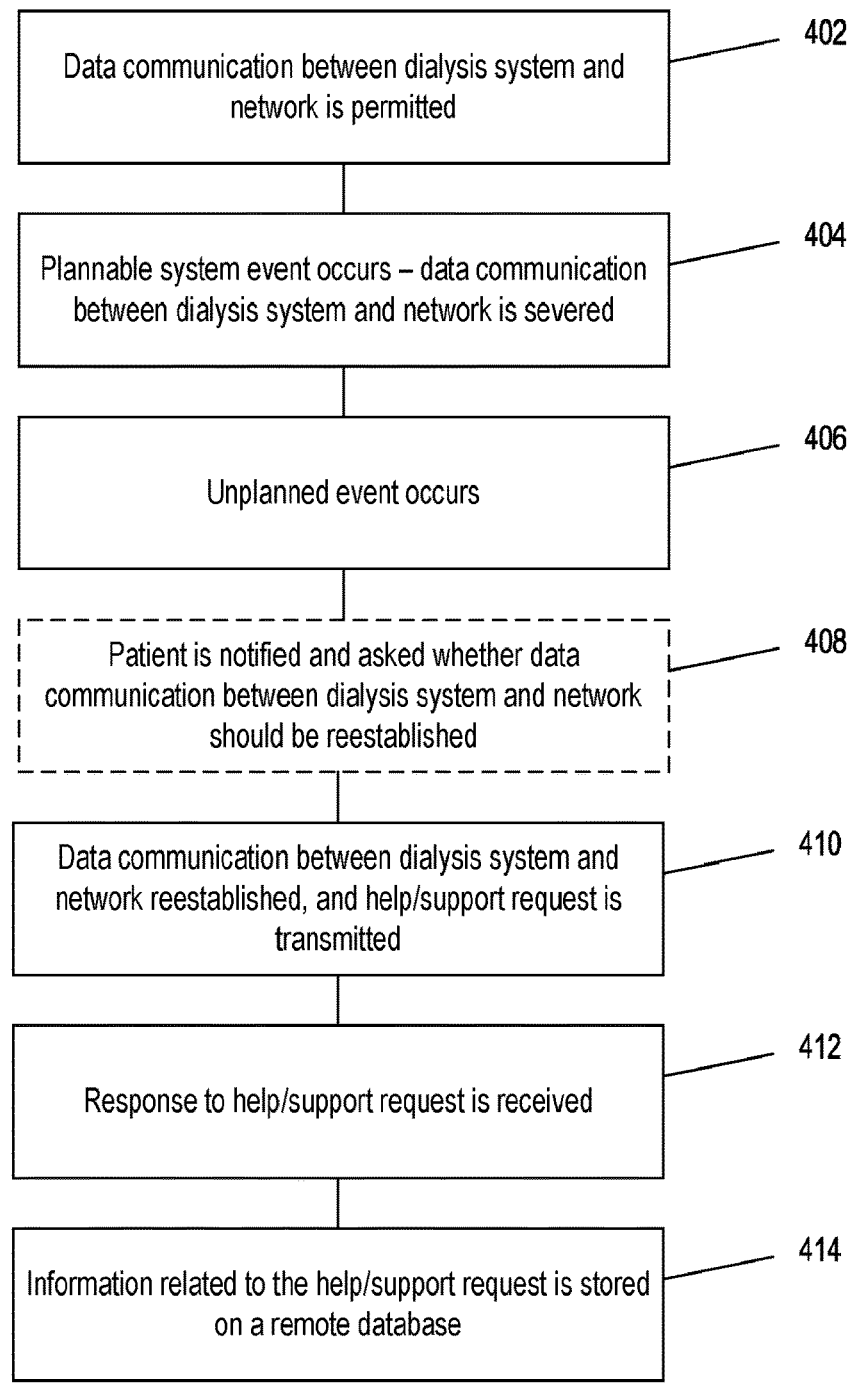
FIG. 4 shows a flowchart of an example process that is performed by the CH system of FIG. 1.

FIG. 4 shows a flowchart of an example process 400 that may be performed by the CH system 100 to enable/disable communications at certain times before, during, or after a treatment by the dialysis system 110.

At 402, the data allowance and limitation unit 302 of the gateway device 120 is in the closed state, thereby permitting data communication between the dialysis system 110 and the network 130. Data communication may be permitted, for example, prior to a treatment commencing. In some implementations, data communication may be permitted before preparations are made for a treatment. Thus, the dialysis system 110 may be allowed to communicate over the network 130 to, for example, obtain a treatment prescription from an external system.

Figure 3B:
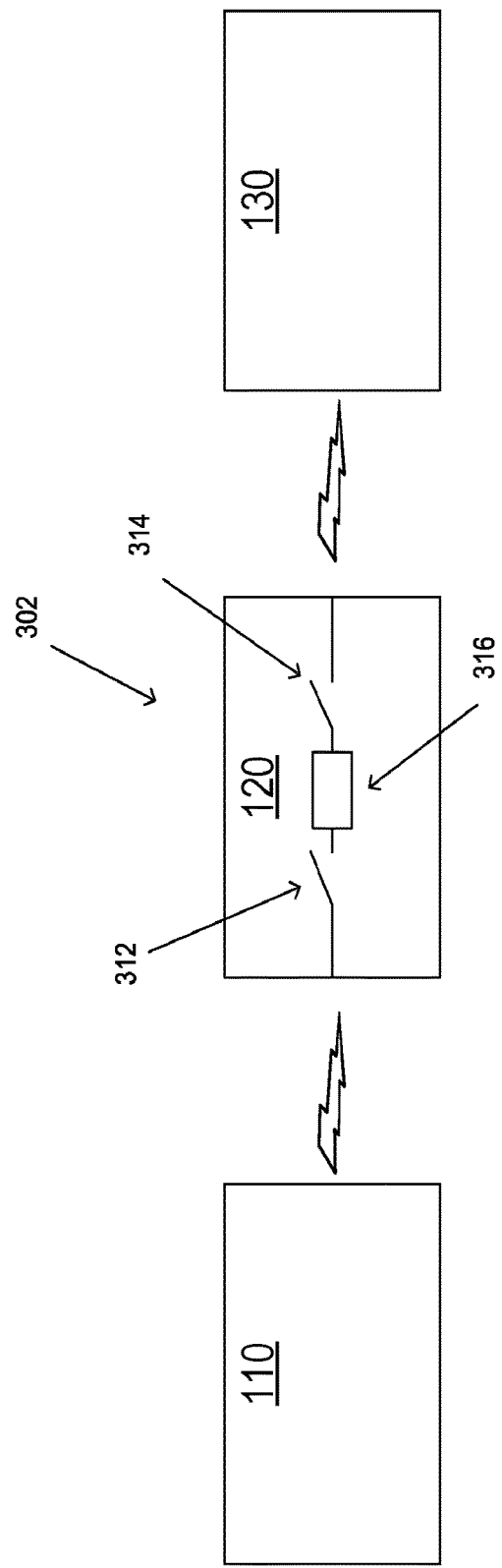

At 404, a plannable system event occurs, and data communication between the dialysis system 110 and the network 130 is severed. In some implementations, data communication is severed by deactivating a communication module of the dialysis system 110 and/or the gateway device 120. Such plannable system events can include connecting a patient to the dialysis system 110, providing medical therapy by the dialysis system 110, and/or connecting/installing disposable components to the dialysis system 110. In particular, when a plannable system event occurs, the data allowance and limitation unit 302 of the gateway device 120 moves from the closed state to the open state, thereby physically severing data communication between the dialysis system 110 and the network 130. In some implementations, the gateway device 120 can operate as an airlock. Referring to FIG. 3B, in some implementations, rather than a single physical switch (e.g., as illustrated in FIG. 3A), the data allowance and limitation unit 302 can be implemented as an airlock in which data can be exchanged between a temporary data buffer 316 located in between two gates 312, 314 of the gateway device 120, thereby allowing for a physical disconnection of data communication, and the dialysis system 110 in case that the first gate 312 is opened and the second gate 314 is closed. On the other hand, data exchange between the temporary data buffer 316 and the network 130 can be achieved only if the first gate 312 is physically closed and the second gate 314 is open. In some implementations, the request can be temporarily saved on the temporary data buffer 316 before it is sent to its destination. In some implementations, the gates 312, 314 are electronically controllable switches. Using such an approach, the dialysis system 110 is not exposed directly to the network 130 during planned operations, thereby improving safety from a cyber-security perspective for both the dialysis system 110 and patients.

In some implementations, a notification may be provided to indicate that data communication between the dialysis system 110 and the network 130 is severed. Such notifications may include acoustical, optical, and/or tactile signals. Similarly, when data communication is enabled, a notification may be provided, thereby allowing the possibility for cyber incidents to be detected quickly. The notification system may also be used to notify the patient and/or technician, clinicians, etc., of unplanned events prior to reestablishing data communication, as described in more detail below.

At 406, an unplanned event occurs, and data communication between the dialysis system 110 and the network 130 is recommended to be reestablished. Such unplanned events may include events during which data communication between patients and doctors, nurses, technicians, or other healthcare service providers is crucial even though the dialysis system 110 is currently in a plannable system event state where data communication is typically prohibited or limited. For example, before, during, or after medical therapies, patients may require immediate support/help by professionals. Thus, such unplanned event-triggered reestablishment of data communication can allow for patients to receive critical help. Possible reasons for proposing and allowing for at least limited data communication may include the following unplanned events: a patient needing further instructions for the preparation/use of medical equipment, the medical system sensing/recognizing/predicting any type of faulty use of medical equipment and recommends support by a medical professional or technician, the medical system sensing/recognizing/predicting a critical health condition of the patient before, during, or after medical therapy and recommending support, the medical system sensing/recognizing/predicting a technical problem, and/or the medical system sensing/recognizing/predicting a complication potentially leading to critical health conditions of the patient. When an unplanned event occurs, a recommendation is made to reestablish data communication between the dialysis system 110 and the network 130.

In some implementations, when the unplanned event occurs, data communication between the dialysis system 110 and the network 130 is recommended to be reestablished based on user input (e.g., the user interacting with a touch button on a user interface). In some implementations, the recommendation is automatic (e.g., in response to the system identifying an unsatisfactory condition).

Optionally, at 408, the dialysis system 110 or a notification system of the dialysis system 110 may notify the patient of the unplanned event and ask whether data communication between the dialysis system 110 and the network 130 should be reestablished such that a medical professional or a technician can be contacted for support. The notification can include optical, acoustical, tactile, or other perceptible signals. The patient is given an option to accept or decline such a recommendation. If the patient accepts the recommendation, the flow proceeds. In some implementations, the patient can accept or decline the recommendation via any type of user interface of the gateway device 120 and/or the dialysis system 110, including physical or virtual buttons for manual acknowledgments, cameras for gesture control, voice command, or other types of input/output interface as described above with respect to FIG. 2 (e.g., the touch screen display 218 or the control buttons 220 of the dialysis system 110, the microphone 250 of the gateway device 120, a microphone of the dialysis machine, etc.).

In some implementations, patient may initialize data communication by themselves so that open questions or possible concerns can be discussed with a medical professional or technician. That is, the dialysis system 110 may not necessarily detect an unplanned event automatically, yet the patient may reestablish data communication between the dialysis system 110 and the network 130. The patient can reestablish the data communication, for example, by interacting with the user interface, which then causes the physical switch to move into the closed state, or by physically interacting with the switch to place it into the closed state directly.

In some implementations, if the patient does not respond to the request for input, the flow may automatically proceed (e.g., the data communication between the dialysis system 110 and the network 130 may be automatically reestablished). This may be the case, for example, if a patient repeatedly shows no reaction to the recommendation to contact a medical professional or technician, or if the dialysis system 110 senses irregularities in the patient's vital parameters (e.g., blood pressure, body temperature, heart rate, oxygen level, respiratory rate, eye movement, skin conductivity, or facial expression). In this regard, one or more cameras or other sensors (e.g., radar sensors) may be included in the dialysis system 110 and/or the gateway device 120 to sense such parameters.

At 410, data communication between the dialysis system 110 and the network 130 is reestablished, and a help/support request is transmitted. In some implementations, such reestablishment of data communication occurs without necessarily needing input from the patient as illustrated at step 408 (e.g., reestablishment of data communication occurs automatically). In some implementations, after an acoustical, optical, and/or tactile countdown, the data communication is reestablished if no input is provided by the patient, and a request for help/support is transmitted via the network 130 to an external system such as a medical facility (e.g., one of the external system illustrated in FIG. 1).

In some implementations, a data package comprising the help/support request is encrypted end-to-end. Possible encryption technologies may include AES, RSA, TripleDES, and/or Twofish, and may further comprise both classical and/or advanced key distribution protocols using, for example, quantum cryptography protocols such as BB84. In some implementations, the data package includes a plurality of additional system and patient information, thereby allowing for a real-time assessment of the patient's and/or the dialysis system's 110 status. Such system and/or patient information may be processed by a human being and/or automatically by a computing device (e.g., a medical server). In some implementations, such system and/or patient information can be processed at the same location where the dialysis system 110 is situated (e.g., at the home of the patient). In some implementations, such information may include digital labels assigned to the help/support request, and/or associated scores that may assist in routing the help/support request to the proper recipient. Such information can help the medical professional or technician receive useful information that provides an overview of the situation at the patient's location. One or more advanced data processing algorithms may be employed to assist with routing such help/support requests, and may use machine learning, deep neuronal networks, etc.

At 412, a response to the help/support request is received. Based on information relying on the help/support data package, the medical professional or technician can decide to choose from a plurality of actions, such as setting the dialysis system 110 into a safe state, sending a request for off-site maintenance, sending a request for video/telephone communication, calling an ambulance, calling a technician for on-site maintenance, sending/providing new medical equipment, adapting/proposing for an adaption to the medical therapy, recommending drugs/agents to improve health conditions of the patient, supporting the patient to handle the dialysis system 110, and/or allowing the dialysis system 110 to be placed in a state for remote control to perform/complete a treatment.

In some implementations, such actions in response to the help/support request can be approved by the patient before they are allowed to occur. In some implementations, the medical professional or technician providing the response to the help/support request may be asked to verify his/her identity using one or more techniques, including using an ID card, scanning a flicker code, scanning a bar code, entering a password, using a biometric input (e.g., fingerprint, handprint, face detection, voice detection, iris detection, etc.).

In combination with the help/support request, a unique incident identifier may be generated, ensuring that only responsible and authorized persons can initiate any combination of actions discussed herein. In consequence, the patient can receive an acoustical, optical, and/or tactile signal that a verified and skilled person wishes to gain remote access providing help/support. If the severity of the incident is extreme, or if a determination is made that the patient is in dire medical state (e.g., unconscious), data communication may be allowed without the prior consent of the patient so that first aid can be administered relatively quickly.

At 414, information related to the help/support request is stored on a remote database (e.g., one of the external systems shown in FIG. 1). Gathered data can be processed, evaluated, and assessed with respect to their origin, the reaction of the medical professional or technician, and the outcome for the patient and/or dialysis system 110 in order to avoid/mitigate future risks, improve healthcare services, and optimize therapy outcomes.

Some example implementations of the process 400 of FIG. 4 will now be described.

Example 1

A patient is receiving dialysis at home. Communication between the dialysis system 110 and the network 130 is severed during treatment. The patient accidentally dislodges the needle, thereby losing small amounts of blood. The dialysis system 110 senses the reduced influx of blood and displays a warning message accompanied by a recommendation to consult a clinician. The patient confirms the recommendation by using a voice command or pressing a virtual/physical button. Data communication between the dialysis system 110 and the network 130 is reestablished. A responsible clinician receives the call for support on a tablet computer, authenticates herself/himself using a fingerprint sensor, and enters instructions to stop the dialysis session and to initialize a communication channel for further discussions. The medical system notifies the patient that a verified clinician wishes to take these actions. The patient acknowledges the request whereupon the dialysis session stops, and a communication channel opens.

Example 2

A patient is receiving peritoneal dialysis. Communication between the dialysis system 110 and the network 130 is severed during treatment. The patient notices an unfamiliar noise emitted by the cycler. Even though the dialysis system 110 does not recommend any support/help, the patient undergoing renal therapy remains concerned and wishes to discuss the issue with a skilled technician. After requesting technical support using voice command (e.g., via the gateway device or the dialysis machine itself), data communication between the dialysis system 110 and the network 130 is reestablished, and a remote technician receives a request for system analysis. Using an ID card, the technician identifies herself/himself and confirms to do a quick off-site check of some essential cycler functions. The patient confirms the request for off-site maintenance and can discuss the issue he/she currently faces.

Example 3

A patient is receiving peritoneal dialysis. Communication between the dialysis system 110 and the network 130 is severed during treatment. During the treatment, a patient suddenly suffers a circulatory collapse reasoned by cardiac arrhythmias. The medical system senses irregularities in the heart rate and significantly decreased blood pressure. After asking for any vital sign from the patient, a counter starts from ten seconds backward before data communication is ultimately established due to lack of response. In a hospital, a doctor receives a help/support request by the medical system with a high urgency ranking (e.g., because immediate actions are required). The doctor instructs to send an ambulance to the patient's location and initiates remote access as the patient can no longer confirm the intended actions of the doctor. Once connected, the doctor can stop the peritoneal dialysis device, and starts monitoring the patient. The doctor then provides paramedics with useful information on the health status of the patient.

While certain implementations have been described, other implementations are possible.

While the medical treatment system has largely been described as being a dialysis system, and in particular a peritoneal dialysis (PD) system, and even more particularly a home PD system, other medical treatment systems can employ the techniques described herein. Examples of other medical treatment systems include another type and/or configuration of PD system, hemodialysis (HD) systems, hemofiltration systems, hemodiafiltration systems, apheresis systems, and cardiopulmonary bypass systems, located at a patient's home or elsewhere.

While the data allowance and limitation unit has largely been described as having two states (e.g., an open state and a closed state), in some implementations, additional states may be provided. For example, rather than the open state corresponding to prevented data communication and the closed state corresponding to allowed data communication, there may be states in which certain types of data are allowed to be transmitted and/or data having less than a threshold size are allowed to be transmitted when the data allowance and limitation unit is in the open state, or when the data allowance and limitation unit is in a third state (e.g., an intermediate state). Thus, in some implementations, the open state can be defined relative to the closed state.

In some implementations, the closed state allows the exchange of more data than the open state. More data can be conceptualized as one or both of more quantitatively (e.g., more bytes per second) or qualitatively (e.g., more types of data can be transmitted). For example, this could range from unlimited data exchange (e.g., no restrictions regarding quantity or data type) vs. no data exchange at all (all data communication is prevented); various limitations with regard to the data type and/or size (e.g., only vital data and/or device data can be transmitted while in the open state or while in another state).

In some implementations, the data allowance and limitation unit is configured to allow the transmission of a first subset of data types and/or data sizes when the data allowance and limitation unit is in the open state and allow the transmission of a second subset of data types and/or data sizes when the data allowance and limitation unit is in the closed state, wherein the second subset is larger than the first one. For example, in some implementations, the first subset of data (e.g., which is allowed to be transmitted while in the open state) can include patient vital data (e.g., heart frequency, blood pressure, body temperature, breathing frequency, etc.). In some implementations, the second subset of data (e.g., which is allowed to be transmitted while in the closed state) can further include video stream data (e.g., including a conversation between the patient and a healthcare professional).

Figure 5:
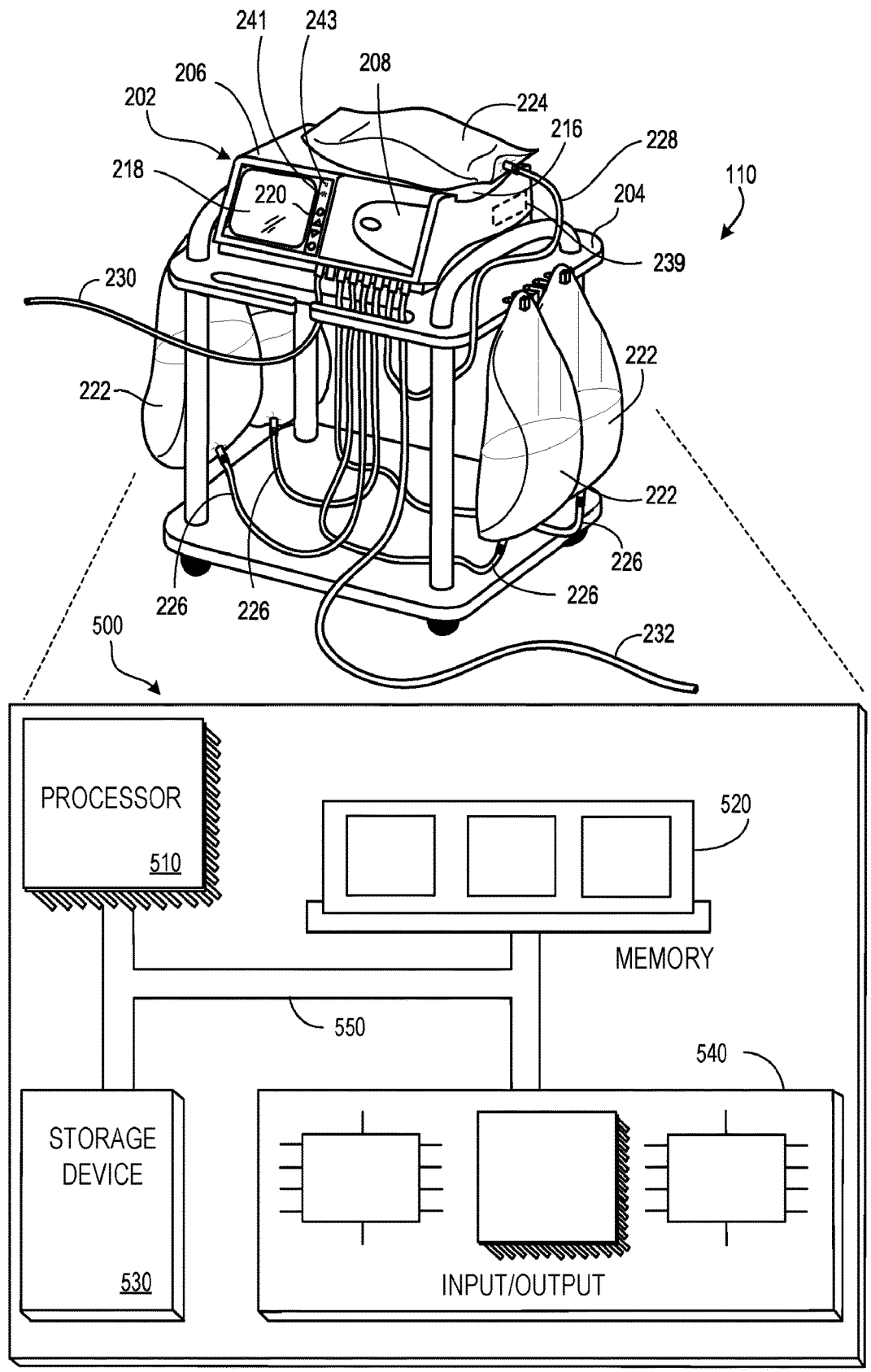
FIG. 5 shows an example of a computer system.

FIG. 5 is a block diagram of an example computer system 500. For example, the various electronic devices/systems described herein may be examples of, or may include one or more examples of, the system 500. The system 500 includes a processor 510, a memory 520, a storage device 530, and an input/output device 540. Each of the components 510, 520, 530, and 540 can be interconnected, for example, using a system bus 550. The processor 510 is capable of processing instructions for execution within the system 500. The processor 510 can be a single-threaded processor, a multi-threaded processor, or a quantum computer. The processor 510 is capable of processing instructions stored in the memory 520 or on the storage device 530. The processor 510 may execute operations such as causing the systems to carry out functions related to voice (e.g., non-touch) communication.

The memory 520 stores information within the system 500. In some implementations, the memory 520 is a computer-readable medium. The memory 520 can, for example, be a volatile memory unit or a non-volatile memory unit.

The storage device 530 is capable of providing mass storage for the system 500. In some implementations, the storage device 530 is a non-transitory computer-readable medium. The storage device 530 can include, for example, a hard disk device, an optical disk device, a solid-date drive, a flash drive, magnetic tape, or some other large capacity storage device. The storage device 530 may alternatively be a cloud storage device, e.g., a logical storage device including multiple physical storage devices distributed on a network and accessed using a network.

The input/output device 540 provides input/output operations for the system 500. In some implementations, the input/output device 540 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices (such as the touch screen display 218 of FIG. 2). In some implementations, mobile computing devices, mobile communication devices, and other devices are used.

In some implementations, the system 500 is a microcontroller. A microcontroller is a device that contains multiple elements of a computer system in a single electronics package. For example, the single electronics package could contain the processor 510, the memory 520, the storage device 530, and input/output devices 540.

Although an example processing system has been described in FIG. 5, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of what has been described herein. Accordingly, other embodiments are within the scope of the following claims.

What is claimed is:

1. A medical system, comprising:
a medical machine; and
a gateway device configured to communicate with the medical machine to allow access to a network, the gateway device comprising a data allowance and limitation unit that is configured to limit communication between the medical machine and the network when the data allowance and limitation unit is in an open state,
wherein the data allowance and limitation unit is placed in the open state when a plannable system event occurs, and
wherein the medical machine is configured to
detect an occurrence of an unplanned event while the plannable system event is being performed, and in response,
cause the data allowance and limitation unit to switch from the open state to a closed state, thereby providing less limited communication between the medical machine and the network compared to the open state.

2. The medical system of claim 1, wherein the plannable system event is regarding a medical treatment that the medical machine performs on a particular patient, and wherein the medical machine is further configured to:
in response to detecting the unplannable event, present one or more questions to the particular patient, and
cause the data allowance and limitation unit to automatically switch to the closed state in response to receiving no response from the particular patient within a predetermined time from when the one or more questions were presented.

3. The medical system of claim 1, further comprising a notification system, wherein the notification system is configured to notify a user of the medical system about the unplanned event by providing a notification that is acoustical, optical or tactile.

4. The medical system of claim 1, wherein the plannable system event is regarding performing a medical treatment on a particular patient, and
wherein in response to detecting the unplanned event, the medical system is configured to present to the particular patient an option to accept or decline a recommendation to establish a communication between the medical machine and the network.

5. The medical system of claim 4, further comprising a user interface through which the particular patient can accept or decline the recommendation.

6. The medical system of claim 4, wherein if the particular patient does not respond to the recommendation, the data allowance and limitation unit moves into the closed state and establishes a communication between the medical machine and the network.

7. The medical system of claim 6, wherein the data allowance and limitation unit switches to the closed state automatically if the medical system senses irregularities in the particular patient's vital parameters.

8. The medical system of claim 1, wherein the medical system is configured to allow a user to cause establishing a communication between the medical machine and the network during the plannable system event.

9. The medical system of claim 8, wherein the communication connects the medical machine to a remote device of one or more of a health provider or a technician.

10. The medical system of claim 9, further comprising a user interface allowing the user to communicate with the health provider or the technician.

11. The medical system of claim 8, wherein the user causes establishing the communication between the medical machine and the network by interacting with a user interface of the medical system, which causes the data allowance and limitation unit to move into the closed state, or by interacting with the data allowance and limitation unit directly to cause it to move into the closed state.

12. The medical system of claim 1, wherein the data allowance and limitation unit is a hardware switch.

13. The medical system of claim 1, wherein the plannable system event comprises one or more of connecting a patient to the medical system, providing medical therapy by the medical system, or connecting or installing disposable components to the medical system.

14. The medical system of claim 1, wherein the unplanned event comprises one or more of a patient needing assistance for preparation or use of the medical system, the medical system sensing a faulty use of medical equipment, the medical system sensing a specific health condition of a patient before, during, or after a medical therapy that the medical system performs on the patient, the medical system sensing a technical problem, or the medical system sensing a complication that potentially leads to one or more specific critical health conditions of the patient.

15. The medical system of claim 1, wherein the data allowance and limitation unit is physically and/or electronically controllable by a user.

16. The medical system of claim 1, wherein the medical system is a dialysis system and the medical machine is a dialysis machine.

17. The medical system of claim 16, wherein the dialysis system is a home dialysis system and the dialysis machine is a home dialysis machine.

18. The medical system of claim 16, wherein the dialysis system is a hemodialysis or peritoneal dialysis system, and the dialysis machine is a hemodialysis or peritoneal dialysis machine.

19. A method performed by a medical system, the method comprising:
  communicating, by a medical machine of the medical system, with a gateway device to allow access to a network, the gateway device comprising a data allowance and limitation unit that is configured to limit communication between the medical machine and the network when the data allowance and limitation unit is in an open state;
  placing the data allowance and limitation unit into the open state when a plannable system event occurs; and
  detect an occurrence of an unplanned event while the plannable system event is being performed, and in response,
  causing the data allowance and limitation unit to switch from the open state to a closed state, thereby providing less limited communication between the medical machine and the network compared to the open state.

20. A connected health system comprising:
  a medical system, comprising:
    a medical machine; and
    a gateway device configured to communicate with the medical machine to allow access to a network, the gateway device comprising a data allowance and limitation unit that is configured to limit communication between the medical machine and the network when the data allowance and limitation unit is in an open state,
  wherein the data allowance and limitation unit is placed in the open state when a plannable system event occurs, and
  wherein the medical machine is configured to
    detect an occurrence of an unplanned event while the plannable system event is being performed, and in response,
    cause the data allowance and limitation unit to switch from the open state to a closed state, thereby providing less limited communication between the medical machine and the network compared to the open state; and
  one or more remote systems configured to communicate with the medical machine when the data allowance and limitation unit is in the closed state.

* * * * *